US00PP36193P3

(12) United States Plant Patent
Hansen

(10) Patent No.: US PP36,193 P3
(45) Date of Patent: Oct. 8, 2024

(54) ***CAMPANULA* PLANT NAMED 'Twilight'**

(50) Latin Name: *Campanula carpatica*
Varietal Denomination: Twilight

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 18/445,829

(22) Filed: Feb. 23, 2024

(65) Prior Publication Data

US 2024/0292771 P1 Aug. 29, 2024

Related U.S. Application Data

(60) Provisional application No. 63/576,689, filed on Feb. 27, 2023.

(51) Int. Cl.
*A01H 5/02* (2018.01)
*A01H 6/26* (2018.01)

(52) U.S. Cl.
USPC ..... Plt./414

(58) Field of Classification Search
USPC ..... Plt./414
See application file for complete search history.

*Primary Examiner* — Susan McCormick Ewoldt

(57) ABSTRACT

A new and distinct Bellflower, *Campanula* plant named 'Twilight' with a dense, compact, mounded habit; cordate to deltoid dark-green foliage and numerous medium purplish-blue campanulate flowers with pale bluish centers flowering for about 14 weeks beginning late spring and continuing until hard frost. The new plant is suitable for landscaping as a specimen, en masse, or in containers.

1 Drawing Sheet

Botanical designation: *Campanula carpatica.*
Cultivar denomination: 'Twilight'.

STATEMENT REGARDING PRIOR DISCLOSURES UNDER 37 CFR 1.77(b)(6)

The claimed plant was first briefly described with a photograph on Dec. 1, 2023, on a website operated by Walters Gardens, Inc. Walters Gardens, Inc. obtained the new plant and all information about the new plant from the inventor. The new plant was first sold in Poland on Feb. 27, 2022, by Danziger who obtained the plant and all information relating thereto, from the inventor. No plants of *Campanula* 'Twilight' have been sold, in this country or anywhere in the world nor has any disclosure of the new plant been made more than one year prior the filing date of the provisional application.

BACKGROUND OF THE PLANT

The present invention relates to the new and distinct Bellflower herein also referred to as *Campanula* 'Twilight', by the cultivar name, 'Twilight', or as the new plant. The new plant was derived from a cross made on Jul. 8, 2016, from a plant in a greenhouse research facility in Zeeland, Michigan. The female parent was the proprietary, unreleased, and unnamed selection known only as 15-6-5 (not patented) and the male parent was 'Violet Teacups' U.S. Plant Pat. No. 32,844. The single selected seedling from this cross represented by 'Twilight' was selected from a group of seedlings by the inventor, isolated, compared in subsequent years to other *Campanula* and subsequently found to be different from all cultivars known to the discoverer, and eventually given the breeder code 16-2-1 prior to being assigned a cultivar epithet.

Asexual propagation at the same nursery in Zeeland, MI, USA by basal cuttings has shown 'Twilight' to be stable and reproduce true to type in successive generations since late June 2017.

SUMMARY OF THE PLANT

*Campanula* 'Twilight' has not been observed in all possible environmental conditions. The phenotype may vary slightly with changes in environments such as light intensity, fertility, water availability, etc. without, however any variation in genotype.

*Campanula* 'Twilight' is distinct from all cultivars known to the inventor in the following traits:

1. Small, cordate to deltoid, serrate, dark-green foliage with compact height and dense mounded habit.
2. Flowers are bell-shaped, medium purplish-blue with a pale purplish-blue center, and clustered at the nodes and ends of heavily-branched stems.
3. Long flowering period for about 14 weeks beginning late spring and continuing until hard frost.

Plants of *Campanula* 'Twilight' are most similar to plants of the varieties 'Rapido Blue' (not patented) and 'Blue Clips' (not patented), and 'Delft Teacups' U.S. Plant Pat. No. 31,574.

'Rapido Blue' has a shorter flowering season, less flower coverage in peak flower, the flowers are larger and have a light blue center. 'Blue Clips' has a larger habit and slightly larger flowers with a shorter flowering season. 'Delft Teacups' has bluish flowers that are larger, flatter with shallower cupping, and the center color that is near white.

The female parent has a smaller flower with a slightly darker center. The male parent has darker solid-colored flowers.

BRIEF DESCRIPTION OF THE DRAWINGS

The color drawings illustrate the overall characteristics of *Campanula* 'Twilight' as a five-year-old plant. The colors are as true as reasonably possible given the technology available. The color values may vary slightly depending on light intensity and quality.

DETAILED BOTANICAL DESCRIPTION

Figure 1:
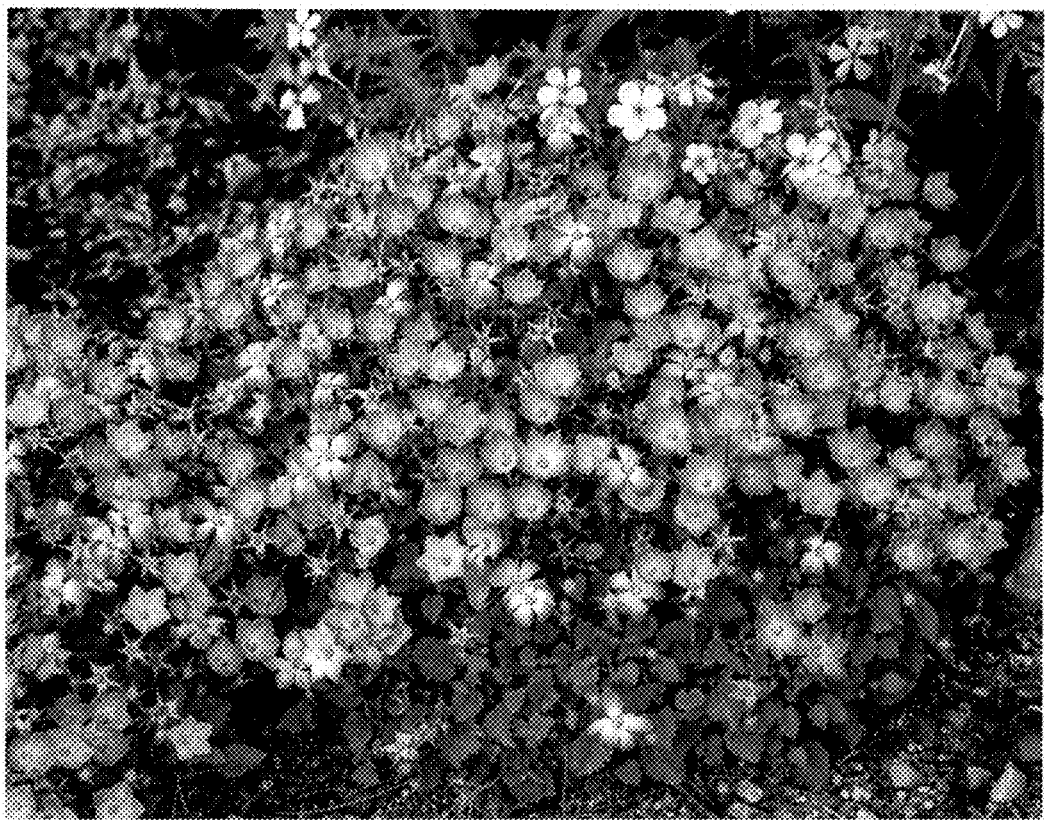
FIG. 1 shows the new plant in a landscape environment.
Figure 2:
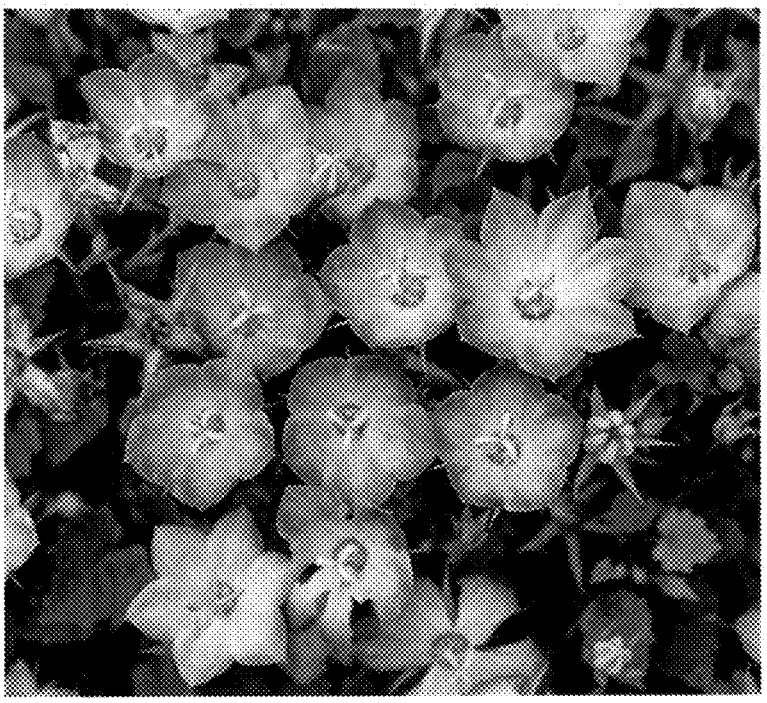
FIG. 2 shows a close-up of the flowers and buds of the new plant.

The following description is based on one and five-year-old plants growing in a full-sun display garden in Zeeland, MI, USA. Except for ordinary dictionary color usage, color references are according to The Royal Horticultural Society Colour Chart, sixth edition, 2015. The new plant has not been observed in all possible growing conditions and may vary in phenotypic characteristics based on water availability, light conditions, fertilizer, temperatures, etc. without varying in genotypic characteristics.

Parentage: Female or seed parent is 15-6-5; the male parent is 'Violet Teacups';

Asexual propagation: Cuttings, about 12 to 20 days to initiate roots; time to finish in a one-gallon container about 12 weeks from an established 25 mm plug;

Plant habit: Rounded mound, herbaceous, perennial, winter-hardy; with about 20 heavily-branched stems up to 50 cm wide and 24 cm tall;

Roots: Finely branched; color nearest RHS NN155B;

Stems: Flexible; glabrous; thin; angular to longitudinally ridged; to about 26 cm long and 3 mm diameter at base;

Stem color: Distally nearest RHS 138A; proximally nearest RHS 146D, no anthocyanins observed;

Leaves: Alternate to semi-opposite; simple; ovate; acute apex; cordate base; margin irregularly serrate teeth; adaxial and abaxial surfaces glabrous, matte; to about 42 mm long and 30 mm wide;

Leaf color: Young expanding leaves adaxial between RHS143A and RHS 144A, abaxial between RHS143A and RHS 144A; mature leaves adaxial nearest RHS 137B, abaxial between RHS 146A and RHS 147B;

Petiole: Thin; concavo-convex; glabrous both adaxial and abaxial; margin entire; to about 45 mm long and 2 mm wide at base;

Petiole color: Nearest RHS 146A adaxial and abaxial between RHS 1348C and RHS 145C;

Veins: Palmate; glabrous; costate abaxial;

Vein color: Adaxial nearest RHS 146D, abaxial proximal midrib nearest RHS 148C, distal midrib and secondary veins between RHS 146A and RHS 147B;

Flower: Single; perfect; complete; campanulate; on terminal branches; to about 25 mm across, about 14 mm long; attitude upright to outwardly;

Inflorescence fragrance: Not detected;

Calyx: Protruding; to about 15 mm wide and 5 mm deep; extending about level with corolla base;

Sepals: Five; divergent; lanceolate; narrowly acute apex; truncate base; margin micro-serrulate; glabrous adaxial and abaxial; about 8 mm long and about 2 mm wide at base;

Sepal color: Abaxial and adaxial nearest RHS 147B;

Flowering period: For about 14 weeks beginning late spring and continuing until hard frost; producing about 160 flowers and 100 buds per plant at one time during peak flowering;

Flower longevity: Individually about 5 to 7 days;

Flower buds: One day prior to opening—ellipsoidal; longitudinally channeled; rounded apex; about 12 mm long and 5.5 mm diameter;

Flower bud color: One day prior to opening—carina nearest RHS 91D, fissures nearest RHS N88D; calyx between RHS 138A and RHS 138B;

Peduncle: About 40 per plant; highly branched; cylindrical to ridged; glabrous; aspect upright to outright; flexible; about 3 mm diameter at base and 30 cm long; about 15 nodes, average internode spacing about 2 cm; branches to about 7.5 cm long and 2 mm diameter at base;

Peduncle color: Nearest 138B;

Pedicel: Cylindrical to striate; glabrous; thin, flexible; to about 20 mm long and 1 mm diameter;

Pedicel color: Nearest RHS 138A;

Petals: Typically five, rarely six or seven; ovate; acute to apiculate apex; basal 9 mm fused; glabrous adaxial and abaxial; margin entire; about 16 mm long and 11 mm wide above fusion;

Petal color: Young adaxial center nearest RHS 91D, distally between RHS N87B and RHS 90C; young abaxial veins and proximally between RHS 91D and RHS 91C, distally nearest RHS 94C; mature adaxial center nearest RHS 91D and distally nearest RHS N87D; mature abaxial veins and proximally nearest RHS 91D, distally between RHS 84D and N87D;

Androecium: Typically five;

*Filament*.—Distally cylindrical, proximally applanate; glabrous; distal portion about 3 mm long and 0.3 mm diameter at base, proximally 2 mm long and 2 mm wide at base; color nearest RHS NN155D distally and nearest RHS 146D proximally.

*Anther*.—Lanceolate; basifixed; about 3 mm long and 1 mm across; color nearest RHS 145C.

*Pollen*.—Not abundant; color between RHS 163C and RHS 163D.

Gynoecium: Syncarpous; half-inferior; about 12 mm long;

*Style*.—Cylindrical; arcuate to reflexed; puberulent distally, glabrous distally; about 8 mm long and 0.5 mm diameter; color nearest RHS 145C.

*Stigma*.—Typically trifid, rarely quad-fid or penta-fid; cochleate distally with maturity; about 5 mm long before curling, 3 mm long when curled, and 0.5 mm diameter; color between RHS 146D and RHS 145C when young maturing to nearest RHS 158C.

Fruit: Oblong poricidal capsule; longitudinally carinate; 8 mm tall and 5 mm wide;

Fruit color: Nearest RHS N200A;

Seed: Flattened ellipsoidal; rounded apex and base; about 1 mm long and 0.5 mm across center;

Seed color: Variable, some seeds between RHS 200A and RHS N200A; *Campanula* 'Twilight' is tolerant of winter temperatures from USDA hardiness at least to zones 3 to 8. The new plant grows best in full-sun with good drainage and adequate moisture. It is not known to be tolerant of diseases and pests that are common to other *Campanula* cultivars.

I claim:

1. A new and distinct cultivar of *Campanula* plant named 'Twilight' as described and illustrated.

* * * * *